US00PP29166P2

(12) United States Plant Patent
Jons

(10) Patent No.: US PP29,166 P2
(45) Date of Patent: Apr. 3, 2018

(54) FLORIBUNDA ROSE PLANT NAMED 'JAJCHEL'

(50) Latin Name: *Rosa hybrida*
Varietal Denomination: JAJchel

(71) Applicant: John Arthur Richard Jons, Houston, TX (US)

(72) Inventor: John Arthur Richard Jons, Houston, TX (US)

( * ) Notice: Subject to any disclaimer, the term of this patent is extended or adjusted under 35 U.S.C. 154(b) by 0 days.

(21) Appl. No.: 15/330,758

(22) Filed: Nov. 4, 2016

(51) Int. Cl.
*A01H 5/02* (2018.01)

(52) U.S. Cl.
USPC ..... Plt./144

(58) Field of Classification Search
USPC ..... Plt./141, 144
See application file for complete search history.

*Primary Examiner* — Susan McCormick Ewoldt

(57) ABSTRACT

A new and distinct variety of medium sized floribunda rose with excellent heat tolerance and strong disease resistance. This rose prolifically produces double to very double, long lasting flowers, throughout the growing season. The flower buds are creamy white and open to form a white flower. Then the petals curve backwards to create a flower with round "cotton ball" like form that is framed in medium green foliage that matures to semi-glossy dark green. This rose exhibits a low, spreading and moderate growth habit that is well suited to providing attractive minimal care and low maintenance ornamentation to the homeowner with a small landscape.

4 Drawing Sheets

Latin name of the plant claimed: *Rosa hybrida.*
Variety denomination: 'JAJchel'.

BACKGROUND OF THE INVENTION

The present invention relates to a new and distinct variety of rose plant of the floribunda commercial class designated 'JAJchel' which originated by crossing 'Prairie Harvest' (unpatented) with an unnamed, undistributed and unpatented seedling.

The primary objective in making the cross that led to this new variety called 'JAJchel' was to invent a new medium sized variety that had the disease resistance and the double blooms of both parents and the demonstrated heat tolerance and prolific clustering bloom habit of the pollen parent.

The new variety was created by artificial pollination carried out in March of 2006 and germinated in January of 2007, in Houston, located in Harris County, Tex., U.S.A. The resulting seedlings were physically and biologically different from each other. The seedlings were grown outside in United States Department of Agriculture cold hardiness zones 9a and were only irrigated with water as needed. In 2010, a superior seedling, 'JAJchel' was identified as meeting the stated objectives and possessing the characteristic of curving it petals backwards towards the hypanthium during the final stage of development leading to an overall globulose flower form.

'JAJchel' was asexually propagated in 2011 by softwood and hardwood cuttings in Houston, Tex., U.S.A, zone 9a. Cuttings were grown successfully in Harris County, Tex., U.S.A, zone 9a and southern Galveston County, Tex., U.S.A, zone 9b. The resulting plants demonstrated that the unique combination of traits of this variety were stable and true to type.

BRIEF SUMMARY OF THE INVENTION

The following traits have been repeatedly observed in 'JAJchel' for a period of five years in Harris and Galveston Counties, Tex., U.S.A. The following attributes in 'JAJchel' distinguish it from its parents as well as from all other varieties of which I am aware:

1) Excellent heat tolerance;
2) Strong disease resistance to black spot, powdery and downy mildew;
3) Continuous flowering throughout the year long south Texas growing season;
4) Doubly to very double medium sized flowers that are borne singularly and in prolific clusters of five or more all year long;
5) Creamy white ovoid buds that open to form an imbricated corolla when semi-mature. Then the petals curve backwards towards the hypanthium during the final stage of development leading to an overall globulose flower form.
6) Long lasting flowers;
7) Medium size with a low, spreading and moderate growth habit;
8) Medium green foliage that turns to a semi-glossy dark green when mature;
9) Ability to root and grow from softwood and semi-hardwood cuttings.

Asexual reproduction of 'JAJchel' by rooting softwood and semi-hardwood cuttings shows that the foregoing and all other characteristics and distinctions come true to form and are established and transmitted through succeeding vegetative propagations.

COMPARISON WITH PARENTS

'JAJchel' is similar to the seed parent 'Prairie Harvest' in demonstrated disease resistance. However, 'JAJchel' differs in the following:

1. 'Prairie Harvest' produces flowers that are large and yellow, whereas 'JAJchel' produces flowers that are white and medium-sized.

2. 'JAJchel' produces flowers that have more petals than 'Prairie Harvest' that stay on the bloom for a longer period of time.
3. 'Prairie Harvest's petals do not curve backwards towards the hypanthium during the final stage of development leading to an overall globulose flower form.
4. 'Prairie Harvest' has a large size and an upright, vigorous growth habit, whereas the 'JAJchel' has a medium size and a low and spreading, moderate growth habit.
5. 'JAJchel' demonstrates greater heat tolerance.

'JAJchel' is similar to the pollen paternal parent in demonstrated disease resistance and heat tolerance. However, 'JAJchel' differs in the following:

1. The paternal parent's flowers are small and light pink, whereas 'JAJchel' flowers are medium sized and white.
2. The paternal parent's petals do not curve backwards towards the hypanthium during the final stage of development leading to an overall globulose flower form.
3. The paternal parent has a small size and upright growth habit, whereas 'JAJchel' has a medium size and a low and spreading growth habit.
4. The paternal parent has light green foliage, whereas 'JAJchel' has medium green foliage that turns to a semi-glossy dark green when mature.

COMPARISON WITH SIMILAR VARIETY

The rose with the greatest similarity to 'JAJchel' is 'Saratoga' (U.S. Plant Pat. No. 2,299, Nov. 12, 1963). Both are floribundas, have ovoid buds and white double flowers that are borne in irregular clusters. The flowers of 'JAJchel' are smaller and have more petals than the flowers produced by 'Sartoga'. 'Sartoga' has thick leathery and stiff petals, whereas 'JAJchel' has thin and satiny petals. 'Saratoga' has an upright, bushy and vigorous growth habit. 'JAJchel' has a low, spreading and moderate growth habit. 'JAJchel' has foliage that is a lighter green and more disease resistant than 'Saratoga'.

BRIEF DESCRIPTION OF THE DRAWINGS

The accompanying photographs were taken of a three year old plant grown on its own roots in Galveston County, Tex., U.S.A. They show as nearly true as it is reasonably possible to make a color photographic illustration of 'JAJchel's character, typical buds, blossoms, foliage and hips.

DETAILED BOTANICAL DESCRIPTION

Figure 1:
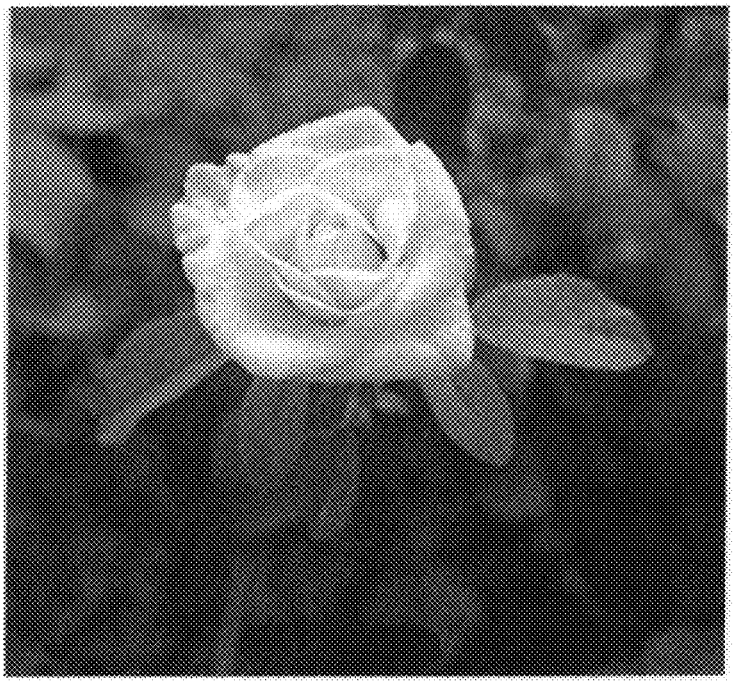
FIG. 1 illustrates a developing flower bud.
Figure 2:
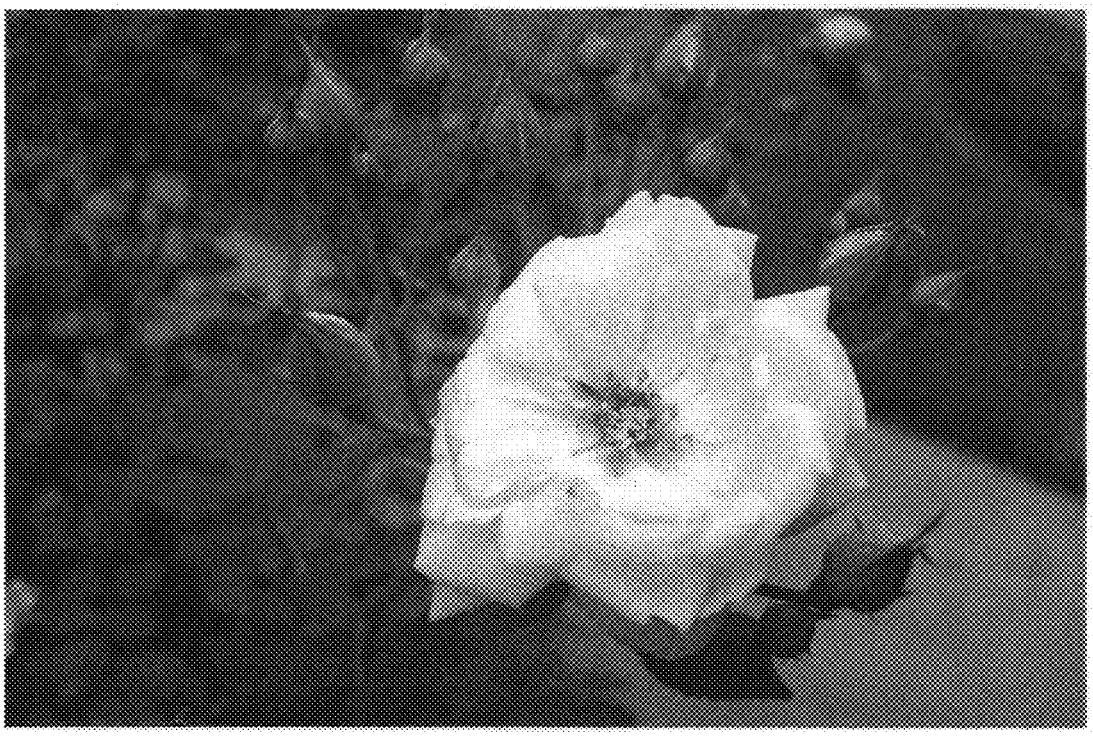
FIG. 2 illustrates a semi-mature flower with an imbricated form.
Figure 3:
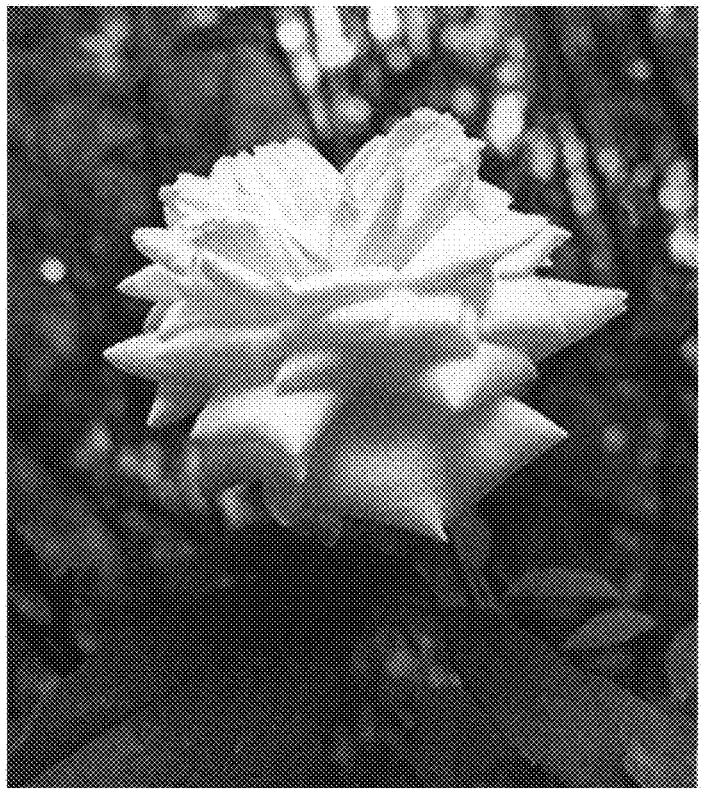
FIG. 3 illustrates a mature flower with the petals curved backwards towards the hypanthium during the final stage of development creating an overall globulose flower form.
Figure 4:
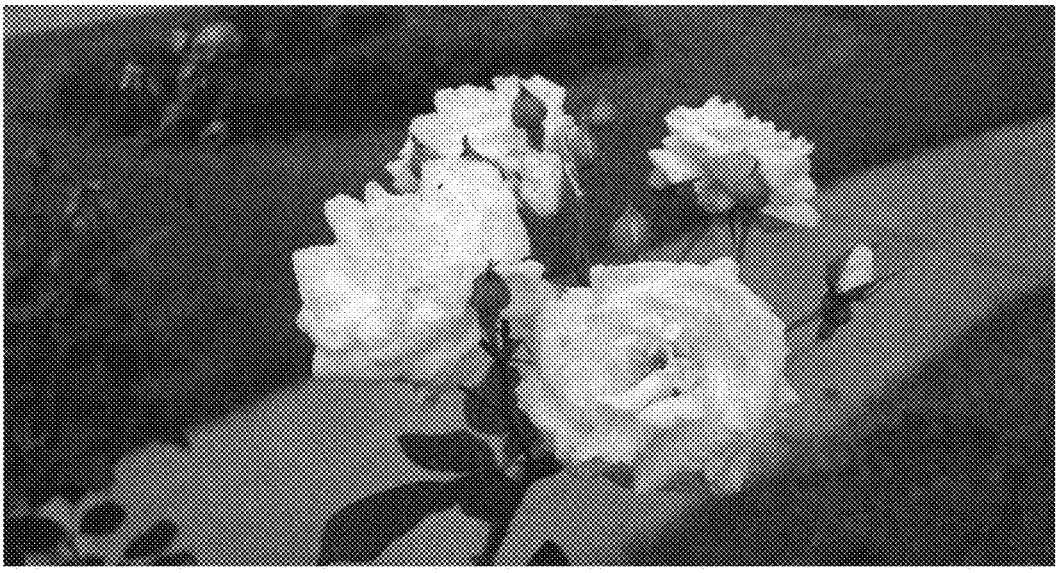
FIG. 4 illustrates an inflorescence of flowers at different stages of development.
Figure 5:
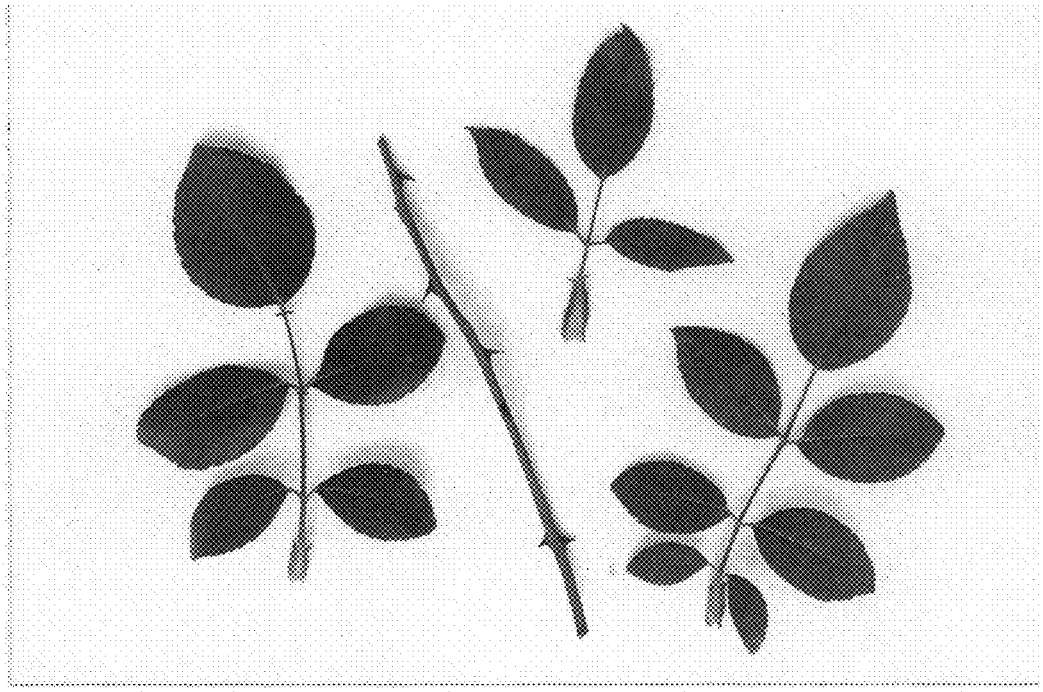
FIG. 5 illustrates leaves with three, five and seven leaflets and a mature stem with prickles.
Figure 6:
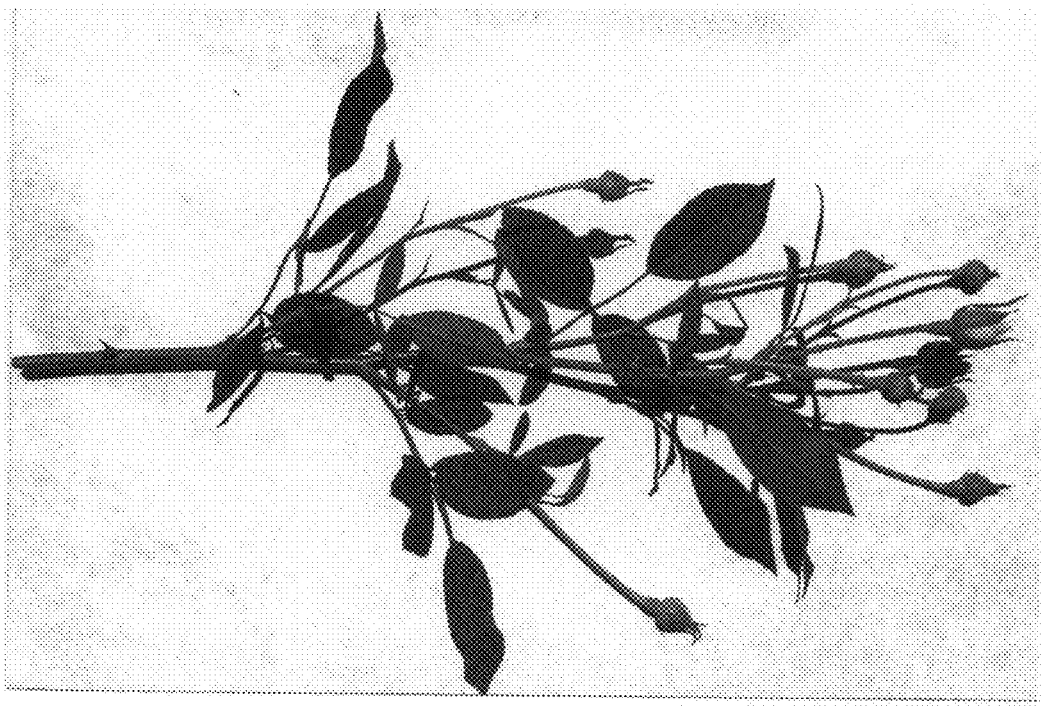
FIG. 6 illustrates an elongated cyme that showcases the flower cluster to a point versus mounded.
Figure 7:
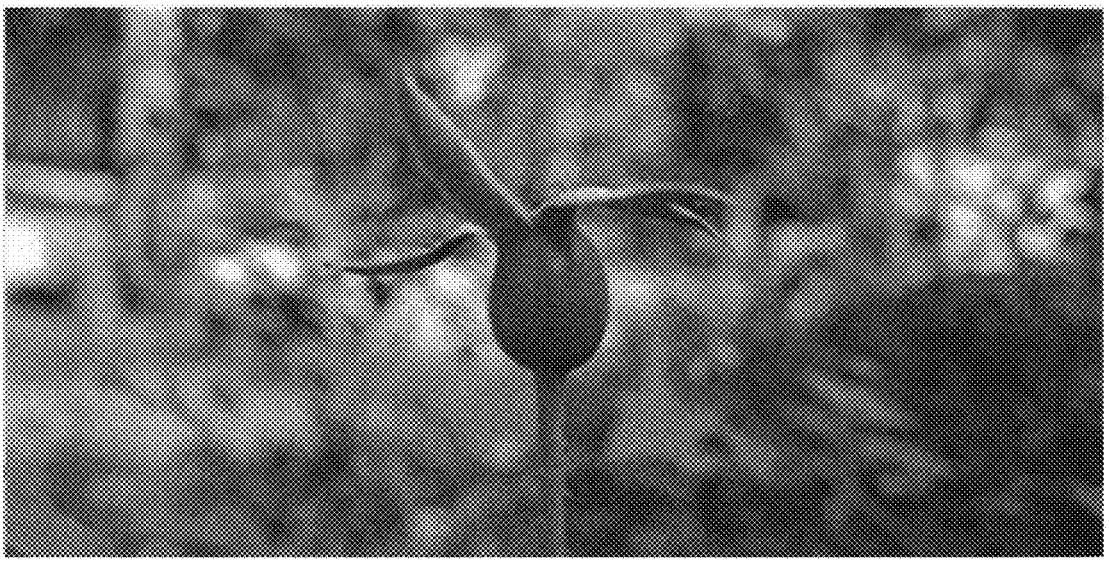
FIG. 7 illustrates a immature green hip.
Figure 8:
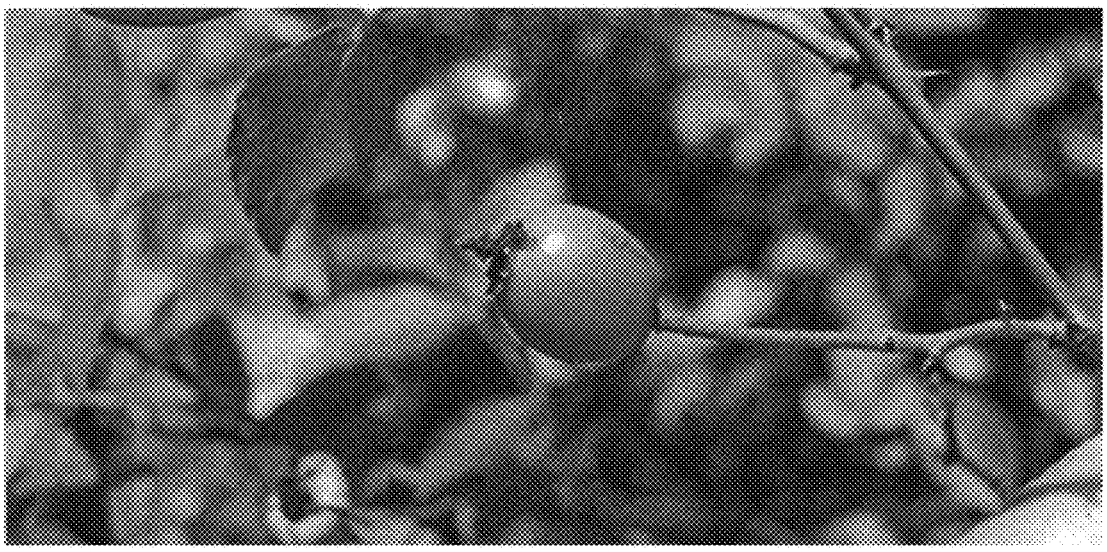
FIG. 8 illustrates a mature orange hip.

The following is a detailed description of my new rose cultivar with color descriptions using terminology in accordance with the The Royal Horticultural Society (London) Colour Chart (1986). The description is based on the observation of three-year-old specimen of the new variety during October 2016 while growing on its own roots in Galveston County, Tex., U.S.A., that was vegetatively propagated from semi-hardwood cuttings in Houston, Tex., U.S.A. Plant part sizes and phenotypic expression may vary somewhat with environmental, cultural and climatic conditions, as well as differences in conditions of light and soil.

Parentage:

*Seed parent*.—'Prairie Harvest' (unpatented), a member of the shrub commercial class of roses.

*Pollen parent*.—Unnamed, undistributed and unpatented seedling, a member of the polyantha commercial class of roses.

Classification:

*Botanical*.—*Rosa hybrida*.

*Commercial*.—Floribunda.

Flower:

Blooming habit: Continuous.

Flower bud:

*Size*.—10 to 15 mm long and 10 to 12 mm in diameter when the petals start to unfurl.

*Form*.—The bud form is pointed.

*Color*.—When sepals first divide, visible petal color is Yellow Group 10D. When half blown and imbricated, the upper or axial sides of the petals are White Group 155B on the distal end and Yellow Group 11D at the proximal end.

*Sepals*.—Color: Yellow-Green Group 144A on the abaxial side and Green Group 138B on the adaxial side. Length: 10 to 20 mm. Width: 4 to 7 mm. Shape: Ovate to broad with some sepals possessing an acuminate tip. The typical number of sepals is five. Surface texture: Adaxial, hoary. Abaxial, generally smooth with very small glandular hairs (<0.1 mm). Sepal margins are lined with fine wooly tomentum, few stipitate glands and hairs. Occasionally there are one or two appendaged sides on the sides of each sepal that are narrow and lanceolate with acuminated tips. Length: 0.5 to 1.0 mm. Width: 0.5 to 0.25 mm.

*Receptacle*.—Color: Yellow-Green Group 144B. Shape: The proximal end is round with a slight increase in width before attachment to the sepals. Size: Small, about 3 to 5 mm wide and 4 to 7 mm long. Surface: Glabrous with sporadic glandular hairs that are comparable to those on the adaxial side of the sepals.

*Peduncle*.—Length: Medium to long typically 18 to 82 mm. Width: Narrow, typically 1 to 2 mm. Surface: Generally glabrous with some small glandulous hairs about 0.1 mm in length. Color: Yellow-Green Group 144B. Strength: Stiff, primarily erect.

Bloom:

*Size*.—Medium. Typical open diameter is 35 to 60 mm.

*Borne*.—Singularly at the end of the stem or in clusters of five or more blooms at the end of an elongated cyme.

*Stems*.—Strength: Medium. Length of flowering stems: Typically about 3.0 to 8.0 cm. Flowering stem diameter: Varies and is typically 1 to 3 mm. Larger stems arising from the base of the plant are about 0.5 to 1.0 cm in diameter while smaller stems arising from secondary or tertiary stems within the plant canopy are typically 3 to 5 mm in diameter. Stem branching: All stems coming from the base of the plant terminate in a primary flowers. Nodes along all the stems typically break to produce stems that range in length and typically produce flowers in an unequally branched compound cyme.

*Form*.—The flower may open informally or with a high center, and then the corolla of a semi-mature flower becomes imbricated. As the flower matures the petals curve backwards towards the hypanthium during the final stage of development leading to an overall globulose flower form.

*Permanence*.—The flowers retain their mature form and their general color tonality to the end and then the petals turn Grey-Orange 164C, and cleanly abscise.

*Petalage*.—Full to very full with 32 to 54 petals and petaloids.

*Color*.—When half blown, the upper or axial sides of the petals are White Group 155B on the distal end and Yellow Group 11D at the proximal end. When fully open and throughout the process of the petals curving backwards to form an overall globoluse flower, the petals are White Group 155D.

*Discoloration*.—Around day seven the petals begin to dry out and turn Grey-Orange 164C depending on temperature and sunlight exposure.

*Fragrance*.—Slight. Character of fragrance: Mild sweet spice.

Petals:

*Texture*.—Thin and satiny to the touch.

*Length*.—1.2 to 3.5 cm.

*Width*.—0.5 to 2.5 cm. Outmost petals tend to be the widest.

*Shape*.—The outermost petals are generally orbicular and the shape of the petals towards the center are generally broadly ovate.

*Margin*.—Entire.

*Apex shape*.—Acute to rounded for the outermost petals and muscronite for the petaloids toward the center of the bloom.

*Base shape*.—Obtuse to acute.

*Arrangement*.—Multiple rows of overlapping petals.

*Petaloids*.—'JAJchel' like a typical rose, has five true petals and between 25 and 45 petaloids that may look like a typical petal. The color of the petal-like portion of the petaloid is typical for the color of a true petal or a more petal-like petaloid without visible anther development.

*Persistence*.—Petals drop off cleanly after drying.

*Lastingness*.—On the plant: Medium (about 7 days). As a cut flower: Moderate (about 6 days).

Reproductive parts:

*Stamens*.—Number per flower: 32 to 48. Anthers — Size: Length before dehiscence: 1.0 to 1.5 mm. Width before dehiscence: Approximately 0.5 mm. Length after dehiscence: 0.75 to 1.0 mm. Width after dehiscence: Approximately 0.25 mm. Color: Before dehiscence: Yellow-Orange Group 17A. After dehiscence: Yellow-Orange Group 22A. Arrangement: Regular around styles. Filaments — Size: Length: 3 to 5 mm. Width: Approximately 0.25 mm. Color: Green-Yellow Group 1B. Pollen Color: Yellow-Orange Group 17A.

*Pistils*.—Number per flower: 16 to 28. Styles — Color: Green-Yellow Group 1B. Length: 3 to 6 mm. Stigmas — Color: Yellow Group 5B. Ovary — Color of immature ovary: Green-White Group 157A.

*Hips*.—Less than 10% of blooms develop into hips. Hypanthium: Color immature: Green Group 146C. Color mature: Greyed-Orange N169B. Shape: Rounded to elongated obovate. Size: 10 to 15 mm long and 10 to 13 mm wide and upon ripening the sepals abscise.

*Achenes* (*ripe*).—Color: Greyed-Orange Group 164C. Shape: Spindle Shaped. Size: 2 to 4 mm long and 1.0 to 1.5 mm wide. Typically there are 7 to 11 achenes per hip.

Plant:

*Form*.—Low growing shrub with a tendency to spread.

*Growth*.—Moderate, well branched and dense.

*Age at maturity*.—3 years.

*Mature plant*.—Height approximately 80 cm and width approximately 120 cm wide.

Leaf:

*Form*.—Leaves are pinnately compound and have three to seven leaflets, with five leaflets being the most common.

*Arrangement*.—Leaves are arranged opposite on the stems.

*Size*.—Small (1.5 to 5.0 cm long and 0.5 to 3.0 cm wide).

*Quantity*.—Normal.

*Leaflet color*.—New foliage: Adaxial side: Green Group 139B. Abaxial side: Green Group 139C. Old foliage: Adaxial side: Green Group 139A. Abaxial side: Green Group 138A.

*Leaflet venation pattern*.—Pinnate reticulate.

*Leaflet venation color*.—The color of the veins is the same or very close to that of the overall leaf blade. New foliage: Adaxial side: Green Group 139B. Abaxial side: Green Group 139C. Old foliage: Adaxial side: Green Group 139A. Abaxial side: Green Group 138A.

*Leaflet size*.—Terminal leaflets: Medium (2 to 5 cm long and 0.5 to 3 cm wide). Non-terminal leaflets: Medium (1.5 to 4 cm long and 0.5 to 2.5 cm wide).

*Leaflet shape*.—Ovate.

*Leaflet base shape*.—The terminal leaflets have rounded leaf bases and the other leaflets have oblique leaf bases.

*Leaflet apex shape*.—Acuminate.

*Leaflet texture*.—Semi-glossy and smooth. On the adaxial side of leaflets the veins are slightly recessed and on the abaxial side they are slightly elevated relative to the general leaf blade.

*Leaflet edge*.—Serrated with typically small-sized single serrations.

*Petiole*.—Color is Green Group 139A.

*Petiole rachis*.—Green Group 139A.

*Petiole underside*.—Generally smooth with periodic small prickles that are 0.25 to 2.0 mm long and 0.25 to 0.75 mm wide and Yellow-Green Group 145A in color.

*Stipules*.—Small, parallel, auricle, facing forward (one is on each side of the petiole) and are 0.4 to 1.5 cm in length and 0.2 to 0.5 cm in width) and sometimes there are several very small serrations (>0.1 to 0.3 mm long) Color: Green Group 139A.

*Disease resistance*.—Very disease resistant to black spot, powdery and downy mildew under observed growing conditions.

*Pest persistence*.—Not observed.

Stems:

*New stems*.—Color: Generally Yellow-Green Group 144B. Bark: Smooth.

*Old wood*.—Color: Generally Yellow-Green Group 147B. Bark: Smooth.

Typical stem prickles:

*Quantity*.—Typically less than average. There is usually one prickle between nodes. Occasionally, there are two prickles between nodes.

*Form*.—Wing shaped and angled downward.

*Length*.—4 to 7 mm.

*Width*.—1.5 to 3.0 mm near the stem and narrowing to the tip.

*Color when young*.—Green Group 138B. New prickles typically have dark red highlights (Greyed-Purple Group 18B) that are more intense on the proximal end of the prickles. These highlights fade as the prickles expand to their mature size.

*Color when mature*.—Brown Group 200C.

Small, secondary stem prickles:

*Quantity*.—Typically none.

Hardiness: 'JAJchel' has not been observed under all possible environmental conditions to date. It has been observed to grow and propagate successfully in United States Department of Agriculture cold hardiness zones 9a and 9b.

I claim:

1. A new and distinct variety of rose plant of the floribunda class, substantially as herein shown and described, characterized by its demonstrated excellent heat tolerance; strong disease resistance to black spot, powdery and downy mildew; continuous flowering throughout the year long south Texas growing season; double to very double medium sized flowers that are borne singularly and in prolific clusters of five or more all year long; creamy white ovoid buds that opens to form an imbricated corolla when semi-mature; petals that curve backwards towards the hypanthium during the final stage of development leading to an overall globulose flower form; long lasting flowers; medium size with a low, spreading and moderate growth habit; medium green foliage that turns to a semi-glossy dark green when mature and the ability to root and grow from softwood and semi-hardwood cuttings.

* * * * *